(12) United States Patent
Behnam et al.

(10) Patent No.: US 10,780,056 B2
(45) Date of Patent: *Sep. 22, 2020

(54) RESVERATROL SOLUBILISATION PRODUCT FOR PHARMACEUTICAL PURPOSES

(71) Applicant: AQUANOVA AG, Darmstadt (DE)

(72) Inventors: Dariush Behnam, Rossdorf (DE); Marshall A. Hayward, Bridgewater, NJ (US)

(73) Assignee: AQUANOVA AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/309,828

(22) PCT Filed: Jan. 26, 2017

(86) PCT No.: PCT/EP2017/051659
§ 371 (c)(1),
(2) Date: Dec. 13, 2018

(87) PCT Pub. No.: WO2017/215791
PCT Pub. Date: Dec. 21, 2017

(65) Prior Publication Data
US 2019/0307700 A1   Oct. 10, 2019

(30) Foreign Application Priority Data

Jun. 14, 2016 (WO) .................. PCT/EP2016/063579

(51) Int. Cl.
| | | |
|---|---|---|
| A61K 31/05 | (2006.01) | |
| A61K 9/48 | (2006.01) | |
| A61K 8/33 | (2006.01) | |
| A61K 9/10 | (2006.01) | |
| A61K 47/26 | (2006.01) | |
| A61K 47/14 | (2017.01) | |
| A61P 1/00 | (2006.01) | |
| A61K 9/00 | (2006.01) | |
| A61K 9/107 | (2006.01) | |
| A61K 47/22 | (2006.01) | |

(52) U.S. Cl.
CPC .......... *A61K 9/4858* (2013.01); *A61K 9/0053* (2013.01); *A61K 9/107* (2013.01); *A61K 9/1075* (2013.01); *A61K 9/4825* (2013.01); *A61K 31/05* (2013.01); *A61K 47/14* (2013.01); *A61K 47/22* (2013.01); *A61K 47/26* (2013.01)

(58) Field of Classification Search
None
See application file for complete search history.

(56) References Cited

U.S. PATENT DOCUMENTS

2013/0309362 A1* 11/2013 Bromley ................... A23L 2/52
426/72
2016/0081976 A1* 3/2016 Bromley .............. A61K 31/355
424/456

OTHER PUBLICATIONS

Yiu Em et al., "An open-label trial in Friedreich ataxia suggests clinical benefit with high-dose resveratrol, with effect on frataxin levels", "J Neurol", doi: 10.1007/s00415-015-7719-2, Apr. 7, 2015, pp. 1344-1353, vol. 262/Iss 5.

Swati Pund et al., "Lipid based nanoemulsifying resveratrol for improved physicochemical characteristics, in vitro cytotoxicity and in vivo antiangiogenic efficacy", "Colloids and Surfaces B: Biointerfaces", May 22, 2014, Publisher: Elsevier B.V., pp. 110-117.

R. Scott Turner et al., "A randomized, double-blind, placebo-controlled trial of resveratrol for Alzheimer disease", "Neurology", DOI 10.1212/WNL.0000000000002035, Sep. 11, 2015, vol. 85/Iss. 16.

Nathan Gray, "Resveratrol could enhance exercise performance", "Journal of Physiology", Jun. 19, 2012, www.nutraingredients.com/content/view/print/648155.

Authorized Officer: Vazquez Lantes, M, International Search Report issued in PCT patent application No. PCT/EP2017/051659, dated Mar. 31, 2017, 3 pp.

Ahmed Amri et al., "Resveratrol self-emulsifying system increases the uptake by endothelial cells and improves protection against oxidative stress-mediated death", "European Journal of Pharmaceutics and Biopharmaceutics", Oct. 31, 2013, Publisher: Elsevier B.V., pp. 418-426.

* cited by examiner

*Primary Examiner* — Kyung S Chang
(74) *Attorney, Agent, or Firm* — Kaplan Breyer Schwarz, LLP

(57) ABSTRACT

A solubilisation product consists of resveratrol, polysorbate 80 and polysorbate 20, at least one medium-chain triglyceride, and tocopherol. The solubilisation product is for use as a pharmaceutical product. The solubilisation product can be used as a pharmaceutical product in the treatment of Alzheimer's disease, Friedreich's ataxia, lysosomal diseases, in particular Tay-Sachs disease, cancer, diabetes, atherosclerosis, heart diseases, arthritis or autoimmune diseases.

14 Claims, No Drawings

RESVERATROL SOLUBILISATION PRODUCT FOR PHARMACEUTICAL PURPOSES

FIELD

The invention relates to a resveratrol solubilisation product for use as a pharmaceutical product. The solubilisation product will make it possible to achieve the high blood plasma levels needed to achieve therapeutic effect for various diseases with significantly reduced, or elimination, of the associated gastro-intestinal side effects shown with natural resveratrol in human clinical trials.

BACKGROUND

Resveratrol is a phytoalexin with antioxidative properties and is a polyphenol. The substance is present, for example, in grapes, in relatively large amounts in the skin of red grapes, but also in raspberries, mulberries, plums, peanuts, and in Japanese knotgrass. Resveratrol can be isolated from grape vines as well. According to the "Wikipedia" online encyclopedia entry, there is some evidence available from in-vitro studies to indicate possible efficacy against cancer cells and beneficial effects in diseases such as atherosclerosis, heart disease, Alzheimer's disease, arthritis, and some autoimmune diseases.

According to a report published in "Pharmazeutische Zeitung Online", issue 29/2007, the anti-oxidative effect of resveratrol is of significance not only for the protection of vessels. As an organ that is particularly rich in lipids, the brain also suffers when exposed to excessive oxidative stress. Accordingly, a neuro-protective effect of resveratrol, which is capable of crossing the blood-brain barrier, was demonstrated in several in-vivo studies in rats. More recent studies even indicate that resveratrol directly promotes the processing of beta-amyloid, which is the pathogenic factor underlying Alzheimer's dementia.

Aside from oxidative stress, chronic low-level inflammation is being discussed as a factor for ageing processes proceeding at an increased rate. According to the report cited above, the intracellular signalling pathway effecting increased production of pro-inflammatory cytokines involves the nuclear factor, kappa-b (NFκ-b). This factor can be activated by a whole range of stimuli (UV radiation, bacterial toxins) and then migrates to the nucleus of the cell, where it induces gene expression of various inflammatory enzymes. NFκ-b is increasingly seen as the crucial switching point linking oxidative and inflammatory processes. Under in-vitro conditions, resveratrol inhibits the nuclear translocation of NFκ-b and thus prevents one of the most important mechanisms in the genesis of pro-inflammatory mediators.

One of the manifold effects of resveratrol is highly specific for this substance. In various organisms, resveratrol has the same life-prolonging effect as sustained calorie restriction (CR). Therefore, it is a member of the CR mimetics.

Likewise, according to Nathan Gray "Resveratrol could enhance exercise performance" (20 Jun. 2012, www.nutraingredients.com/content/view/print/648155) further studies in various organisms indicate that resveratrol has an effect against cancer and diabetes as well as an Alzheimer-protective effect and anti-inflammatory properties and beneficial cardiovascular effects.

However, one issue of known resveratrol formulations is that these show extremely low plasma levels of drug due to absorption and liver metabolism related factors in the body of the patient. It is recognized that micronizing the resveratrol prior to ingestion can improve bioavailability. To increase the circulating drug levels, it is known that to add further components aside from resveratrol to generate carrier systems, such as, for example, emulsions or liposomes, may provide some benefits. Whereas resveratrol is dissolved in a lipophilic phase and is stabilised in the form of droplets in an aqueous environment in emulsions, resveratrol can be retained in a phospholipid layer in liposomes. This can be used to increase the bioavailability as compared to the native form, but formulations of this type, such as liposomes, are mechanically extremely unstable and are not resistant to the milieu predominating in the stomach.

Moreover, for applications of liquid formulations for use in pharmaceutical products, it is disadvantageous that the known formulations are non-transparent and do not produce a clear aqueous solution.

SUMMARY

It is an object of the invention to provide a sufficiently stable formulation for oral administration for use as a pharmaceutical product. Specifically, it is an object of the invention to generate a formulation for the resveratrol agent, in which the bioavailability of resveratrol is appropriate such that it allows for intake of significantly reduced amounts as compared to the amounts of native resveratrol that need to be taken up. The optimisation of the absorption of resveratrol through an appropriately suitable formulation for a pharmaceutical product is one object of the invention in this context. Moreover, it is an object of the invention to attain a stable homogeneous fine distribution of resveratrol in the corresponding pharmaceutical end-products.

The invention provides a micellar resveratrol formulation on the basis of which a markedly higher bioavailability than with native resveratrol was determined. The invention provides a solubilisation product consisting of resveratrol, a mixture of polysorbate 80 and polysorbate 20 as well as at least one medium-chain triglyceride and tocopherol for use as a pharmaceutical product.

The formulation according to the invention generates micelles that are loaded with resveratrol by means of the solubilisation product.

DETAILED DESCRIPTION

It has been shown, surprisingly, that the use of polysorbate 80 alone or of polysorbate 20 alone does not lead to the desired stable micelles, which remain stable even at the extremely acidic conditions existing in the stomach and thus release the resveratrol to the organism no earlier than via the small intestinal wall. Only the use of the two emulsifying agents in combination with at least one medium-chain triglyceride and tocopherol, in particular mixed tocopherols, allowed the inventor to generate a solubilisation product having said stable micelles.

Medium-chain triglycerides (MCTs) are triglycerides containing medium-chain fatty acids. Medium-chain fatty acids include capronic acid, caprylic acid, capric acid, and lauric acid. These are saturated fatty acids, which are present in tropical plant fats such as coconut oil and palm kernel oil. Low fractions of the substances are also present in milk fat. There is no pure MCT oil in nature, but pure MCT oils can be obtained by synthesis. In the scope of the invention, individual MCTs or a mixture of different MCTs can be used as medium-chain triglycerides.

The invention creates the opportunity to implement a resveratrol formulation with a high load of resveratrol in the micelles without the micelles bursting open and releasing the resveratrol as a sediment upon dilution with water.

In the scope of the invention, the content of resveratrol in the solubilisation product according to the invention can be varied up to very high values without destabilising the micelles. The resveratrol content in a preferred embodiment of the solubilisation product is in the range of 3% by weight to 15% by weight, particularly preferably in the range of 5% by weight to 10% by weight, and in particular is 10% by weight.

The amount of the emulsifying agent mixture made up of polysorbate 20 and polysorbate 80 in the solubilisation product according to the invention is in the range of approximately 65% by weight to approximately 95% by weight, in particular in the range of approximately 70% by weight to approximately 92% by weight, particularly preferably the fraction of the emulsifying agent mixture is approximately 71.8% by weight.

In an advantageous refinement, the amount of the at least one medium-chain triglyceride in the solubilisation product is in the range of at least approximately 2% by weight to approximately 8% by weight, in particular in the range of approximately 3% by weight to approximately 5% by weight, whereby the fraction of the at least one medium-chain triglyceride (MCT fraction) preferably is approximately 4.5% by weight.

In another advantageous embodiment of the invention, the amount of tocopherol, in particular mixed tocopherols, in the solubilisation product is in the range of up to approximately 10% by weight. In particular, the amount of the tocopherol content in the solubilisation product according to the invention is in the range of approximately 3% by weight to approximately 6% by weight and preferably the tocopherol fraction is approximately 5.25% by weight.

Depending on the specific application field, the solubilisation product can be produced in the scope of the invention using α-tocopherol and/or β-tocopherol and/or γ-tocopherol and/or δ-tocopherol or using a mixed tocopherols consisting of α-tocopherol, β-tocopherol, γ-tocopherol, and δ-tocopherol.

Compared to the use of, for example, α-tocopherol alone, it has been evident that the use of the same amount of mixed tocopherols imparts a greater anti-oxidative potential to the solubilisation product according to the invention.

Since the micelles are particularly small in the solubilisation product according to the invention, a clear and lastingly transparent product is obtained. The narrow particle size distribution is another contributing factor, since the distribution of the diameters of the micelles at pH 7 and room temperature, i.e. at a temperature in the range of approximately 18° C. to approximately 22° C., ranges only from approximately 1 nm to approximately 25 nm. In particular, on average, approximately 69.45% by volume +/−0.55% by volume of the particles are larger than 3.22 nm +/−0.06 nm, and, on average, approximately 30.55% by volume +/−0.55% by volume of the particles are larger than 12.74 nm +/−1.04 nm.

At pH 1 and a temperature of 37° C., the distribution of the diameters of the micelles ranges from approximately 2 nm to approximately 900 nm. In particular, on average, approximately 60.35% by volume +/−1.25% by volume of the particles are larger than 10.33 nm +/−0.43 nm, and, on average, approximately 31.75% by volume +/−9.15% by volume of the particles are larger than 161.85 nm +/−4.25 nm.

Since the particle sizes are small, the advantageous formation of a clear liquid, in particular for perception by the human eye, is attained.

The micellar particle size distributions characterised above were measured based on the principle of dynamic light scattering using laser light of a wavelength of 780 nm. The particle size measurements were done with the ParticleMetrix NANOFLEX backscatter particle analyser. The measuring principle is based on dynamic light scattering (DLS) in a 180° heterodyne backscatter arrangement. In this geometry, a part of the laser beam is mixed into the scattered light (heterodyne technique). Due to the short light path of 200 micrometers to 300 micrometers in the sample, backscattering is of advantage for absorbing and highly concentrated samples. The heterodyne technique has an amplifying effect on the signal/noise ratio and on the sensitivity of the sub-100 nm-range.

The laser light is coupled into the Y fork of an optical fibre. The laser light that is partially reflected at the sapphire window of the sample chamber and the light scattered backwards by the sample return in the same fibre. The detector in the second branch of the Y fork records the mutually interfering signals. A rapid Fourier transformation analysis decomposes the fluctuating scattered light fractions into a frequency-dependent so-called "power spectrum". Each frequency component is a Brown's diffusion constant and can thus be assigned to a particle size. The Stokes-Einstein formula is used for conversion to a particle size distribution:

$$D = k \frac{T}{3\pi \eta d_P}$$

This equation links the diffusion constant D, Boltzmann constant k, temperature T, dynamic viscosity $\eta$ of the medium, and diameter $d_P$ of the particles. A temperature sensor is attached in the measuring device close to the sample in the vicinity of the sapphire window.

Each of the samples was diluted once 1:10 with fully deionised water. For this purpose, the solubilisation product was dissolved in water while stirring. It dissolves fully in water producing a clear solution. This solution is stable and transparent. Subsequently, the NANOFLEX was used to run three measurements for a period of 30 seconds and the mean of the measured values was calculated.

In addition, the samples were adjusted to pH 1 and then measured again at 37° at otherwise unchanged conditions. This was to simulate physiological conditions in terms of the gastric passage of the solubilised pharmaceutical product.

The clarity of the solubilisation product can also be made evident by its low turbidity.

The following working hypothesis is used for this purpose: The solubilisation is the better, the clearer an aqueous dilution of a solubilisation product or other formulation of resveratrol is, i.e. at a pH value of 1.1 and a temperature of 37° C. The better the solubilisation, the better is the bioavailability of the pharmaceutical product and/or of its resveratrol agent.

This is evident already from the particularly low turbidity of the solubilisation product, which can be understood to be a kind of characteristic parameter for the bioavailability. The turbidity of the solubilisation product according to the invention is less than 50 FNU, measured by scattered light measurement with infrared light according to the provisions of the ISO 7027 standard at a 1:50 dilution of the solubilisation product in water.

The solubilisation product according to the invention retains its low turbidity even after 24 hours of storage at 21° C. and pH 7 and after 1 hour of storage at 37° C. and pH 1.1, i.e. under the storage conditions at room temperature in aqueous dilution and under the conditions during passage through the stomach. Accordingly, it is the current understanding of the inventor that the resveratrol, having passed through the stomach, is still present in the solubilisation product according to the invention in the form of the stable, very small micelles and can therefore be taken up very well in the later digestive tract.

For experimental determination of the turbidity, the turbidity measuring devices are calibrated using a standard suspension. The display therefore does not show the measured light intensity, but the concentration of the calibration suspension. Accordingly, measuring any suspension, the display indicates that the corresponding liquid causes the same light scattering as the standard suspension of the displayed concentration. Formazine is the internationally defined reference standard for turbidity. "FNU", i.e. "formazine nephelometric units", is one of the most common units. This is the unit used, for example, in water treatment for the measurement at 90° C. in accordance with the provisions of the ISO 7072 standard.

The transparent and fully stable water-soluble resveratrol formulation according to the invention comprises, in the absence of the excipients specified above, stable transparency and, moreover, markedly improved bioavailability in pH-independent manner in gelatine-free capsules (hard and/or soft) and in liquid, water-based end-products.

Products comprising said transparency and water solubility, but also, in particular, this high level of bioavailability of the resveratrol formulation, are urgently sought after in the pertinent industry as capsule filling for innovative products. A resveratrol formulation meeting these requirements does not yet exist to the knowledge of the inventor.

By means of the specific formulation, the invention managed to markedly increase the bioavailability as compared to the native form of resveratrol.

The native form of resveratrol has been tested in several human clinical trials with a common denominator that a very high dose, mostly over 2 g daily, is needed to achieve any therapeutic effect. This high dose has clearly shown that it creates unwanted gastro-intestinal side effects, such as abdominal pain and diarrhoea (see Yiu et al, J Neurol 2015 may; 262(5): 1344-53. doi: 10.1007/s00415-015-7719-2. Epub 2015 Apr. 7).

A dose escalation study of resveratrol in Alzheimer's Disease showed a positive result, but only at the high dose of 2000 mg/day (A randomized, double-blind, placebo-controlled trial of resveratrol for Alzheimer disease R. Scott Turner, Ronald G. Thomas, Suzanne Craft, et al. *Neurology* published online Sep. 11, 2015 DOI 10.1212/WNL.0000000000002035). The 2000 mg/day dose was considered the highest dose that would be safe to administer. GI tolerability was the most common AE reported in the study, although this did not lead to excessive patient drop-outs.

Dosing limitations related to tolerability and safety are believed to be the key reason that there is no resveratrol product in the world clinically approved for treatment of any disease.

Due to the inventive formulation in a solubilisation product with very small, stable, and gastric juice-resistant micelles, the invention creates a resveratrol solubilisation product for use in, but not limited to, the treatment of Alzheimer's disease, Friedreich's ataxia and other Ataxia related diseases or neurological disorders, lysosomal diseases, cancer, diabetes, atherosclerosis, heart diseases, arthritis and/or autoimmune diseases.

Circulating plasma levels of resveratrol in the formulations as described have shown a surprisingly high level of circulating resveratrol compared to native resveratrol delivered as suspension or delivery of micronized resveratrol API as a suspension as tested in mice and rats.

For example, a 5% resveratrol solubilisation product based formula show a higher maximal plasma drug level ("Cmax") than resveratrol API from the same source, and micronized resveratrol from another source. The formulation also showed a higher total absorption amount (the "AUC"). A study in rats at a surprisingly high 10% dose loading showed similarly high plasma levels of resveratrol. These test results are summarized below.

Mice were tested for relative plasma bioavailability of resveratrol administered orally from different formulations. At 50 mg/kg resveratrol delivered as the 5% dose loaded solubilisation product, the Cmax (average highest maximum concentration in blood plasma) was 17 fold higher than with unformulated API and more than 10 fold higher than Micronized Mega Resveratrol. Micronized resveratrol showed slightly higher absorption than standard API. When treated at 25 mg/kg, the solubilisation product group showed less than half the resveratrol absorption than the 50 mg/kg dose of the solubilisation product, but was broadly similar to the 50 mg/kg standard suspension treatments.

The AUC (for 4 hours after dosing with 50 mg/kg) was 4 fold higher for the solubilisation product than for the Micronized Mega Resveratrol.

In rats, the 10% dose loaded solubilisation product dosed at 50 mg/kg showed a Cmax was 7 fold higher than the level observed with micronized resveratrol, and the AUC (for 24 hours after dosing) was two and a half fold higher for the solubilisation product than for Micronized Mega Resveratrol.

The terminal elimination rate of resveratrol from the solubilisation product or from Micronized Mega Resveratrol was the same and consists with literature, meaning that the solubilisation product formula does not alter resveratrol metabolism after resveratrol is present in plasma.

In summary, then, the solubilisation product forms of orally administered resveratrol offer superior absorption properties as compared to standard forms. The resveratrol solubilisation product formulas clearly outperformed the non-micellar dosing form. Inter-species dose scaling is consistent with expectations, suggesting a dose reduction exploiting the solubilisation product is achievable in man.

Due to the markedly increased bioavailability of resveratrol in the solubilisation product according to the invention as compared to the native form, the amount of resveratrol to be taken up daily by a patient by oral administration can be reduced. Accordingly, it has been evident, for example, that the administration of 200 mg resveratrol in a solubilisation product according to the invention is sufficient to attain the effect of a daily dose of 3,500 mg native resveratrol. Accordingly, the invention provides the resveratrol solubilisation product described above also for application in a method for the treatment of, but not limited to, Alzheimer's disease, Friedreich's ataxia and other Ataxia related diseases, lysosomal diseases, cancer, diabetes, atherosclerosis, heart diseases, arthritis and/or autoimmune diseases, whereby the solubilisation product is administered, in particular orally, in an amount corresponding to at least 200 mg resveratrol per day. Preferably, an amount of the solubilisation product corresponding to approximately 200 mg resveratrol per day is administered.

In principle, the solubilisation product can be used pharmaceutically both externally by application to skin, nails, and/or hair or internally by uptake into the body. All forms of application for pharmaceutical products shall be available also to the use of the solubilisation product, in particular oral, dermal, intravenous or inhalational administration of the solubilisation product or of a fluid containing the solubilisation product.

It has also been evident to be advantageous that the solubilisation product according to the invention can be provided easily in the form of capsules for oral intake, since it does not attack the capsules. Accordingly, the invention also provides a capsule filled with the solubilisation product, whereby the capsule can be provided as soft gelatine capsule or hard gelatine capsule or as soft gelatine-free capsule or as hard gelatine-free capsule.

A fluid containing the solubilisation product according to the invention, whereby the fluid is a pharmaceutical product, is another dosage form. Specifically, the fluid can comprise an aqueous dilution of the solubilisation product. The usability in a fluid of the solubilisation product according to the invention is not linked to the viscosity thereof; likewise, the solubilisation product can be incorporated into hydrophilic and lipophilic media.

Accordingly, the invention enables a therapeutic method for the treatment of, but not limited to, Alzheimer's disease, Friedreich's ataxia and other Ataxia related diseases, lysosomal diseases, cancer, diabetes, atherosclerosis, heart diseases, arthritis and/or autoimmune diseases, in which the solubilisation product according to the invention is administered to the patient, in particular by oral administration. Due to the increased bioavailability as compared to the native form that can be attained by means of the invention, the daily doses can be markedly reduced in advantageous manner as compared to the oral administration of native resveratrol.

An exemplary embodiment of a solubilisation product according to the invention is illustrated hereinafter.

Exemplary Embodiment

For production of the solubilisation product, only
100 g resveratrol;
45 g medium-chain triglycerides;
600 g polysorbate 80;
180 g polysorbate 20, and
75 g mixed tocopherols
were used.

The resveratrol was (trans-)resveratrol, 99%, CAS number 501-36-0, procured from Bachem AG, Bubendorf, Switzerland. The CAS number is an international reference standard for chemical substance. Each known chemical substance has a unique CAS number.

MCT oil (70/30) Rofetan GTCC 70/30 made by DHW Deutsche Hydrierwerke Rodleben GmbH, Dessau-RoJlau, Germany, CAS number 73-398-61-5, was used as the medium-chain triglycerides.

Commercial preparations such as, for example, TEGO SMO 80 V, Evonik or Crillet 4/Tween 80-LQ-(SG), Croda GmbH, Nettetal, Germany, can be used as polysorbate 80 (E433, CAS number 9005-65-6).

Commercial preparations such as, for example, TEGO SML 20 V, Evonik or Crillet 1/Tween 20-LQ-(SG), Croda GmbH, Nettetal, Germany, can be used as polysorbate 20 (E432, CAS number 9005-64-5). Vitapherole T-70 Non GMO, a 70% mixed tocopherols in plant oil made by Vitae Caps S.A., Spain, or EMix 70 made by Nutrilo GmbH, Cuxhaven, Germany, can be used as mixed tocopherols (E306, CAS numbers 59-02-9, 16698-35-4, 54-28-4, and 119-13-1).

Polysorbate 20, polysorbate 80, mixed tocopherols, and MCT oil were homogenised at a temperature in the range of approximately 18° C. to approximately 22° C. while stirring.

Resveratrol was then added to the mixture of polysorbate 20, polysorbate 80, mixed tocopherols, and MCT oil and heated, while stirring, to a temperature in the range of approximately 83° C. to approximately 87° C. for homogenisation. As soon as the fluid was homogeneous and transparent, it was cooled to a temperature below approximately 30° C.

The resulting solubilisation product is a light brown viscous fluid, which produces a yellowish clear solution when diluted with water at a ratio of 1:50. According to an HPLC analysis, the resveratrol content of the solubilisation product is at least 10% by weight, whereby the resveratrol is enclosed in micelles. According to an aerometer measurement, the density of the solubilisation product is in the range of 1.05 to 1.15 g/cm$^3$ at a temperature of 20° C. The turbidity of the solubilisation product is less than or equal to 50 FNU, solution in water at a ratio of 1:50. Said solution has a pH in the range of 6 to 8 according to a potentiometric determination.

Referring to the use of the solubilisation product according to the invention as pharmaceutical product for oral administration in capsules, it has been evident that a daily dose of three capsule fillings of 675 mg each, corresponding to a total dose of 2,025 mg of the solubilisation product according to the invention, for therapeutic purposes is equivalent to the administration of 3,500 mg of the native form of resveratrol. This amount of the solubilisation product corresponds to approximately 200 mg resveratrol.

It is evident to a person skilled in the art that the invention is not limited to the exemplary embodiments described above, but rather can be varied in manifold ways. Specifically, the features of the individual exemplary embodiments can also be combined with each other or interchanged.

The invention claimed is:
1. A solubilisation product consisting of:
resveratrol;
an emulsifying agent mixture of polysorbate 80 and polysorbate 20;
at least one medium-chain triglyceride (MCT); and
tocopherol or mixed tocopherols,
wherein the solubilisation product is for use as a pharmaceutical product.
2. The solubilisation product according to claim 1, characterised in that:
the fractional amount of the resveratrol is in the range of 3% by weight to 15% by weight, or in the range of 5% by weight to 10% by weight, or is 10% by weight.
3. The solubilisation product according to claim 1, characterised in that:
the fractional amount of the emulsifying agent mixture of polysorbate 20 and polysorbate 80 is in the range of approximately 65% by weight to approximately 95% by weight, or in the range of approximately 70% by weight to approximately 92% by weight, or is approximately 71.8% by weight.

4. The solubilisation product according to claim 1, characterised in that:
   the fractional amount of the at least one medium-chain triglyceride is in the range of at least approximately 2% by weight to approximately 8% by weight, or in the range of approximately 3% by weight to approximately 5% by weight, or is approximately 4.5% by weight.

5. The solubilisation product according to claim 1, characterised in that:
   the fractional amount of the tocopherol or the mixed tocopherols is in the range of approximately 3% by weight to approximately 6% by weight, or is approximately 5.25% by weight.

6. The solubilisation product according to claim 1, characterized in that:
   the solubilisation product has micelles wherein a distribution of diameters of the micelles ranges from approximately 1 nm to approximately 25 nm.

7. The solubilisation product according to claim 1, characterised in that:
   a turbidity of the solubilisation product is less than 50 FNU, measured by scattered light measurement with infrared light according to the provisions of the ISO 7027 standard at a 1:50 dilution of the solubilisation product in water.

8. The solubilisation product according to claim 1, characterised in that:
   a turbidity of the solubilisation product after 24 hours of storage at room temperature and pH 7 is less than 50 FNU, measured by scattered light measurement with infrared light according to the provisions of the ISO 7027 standard at a 1:50 dilution of the solubilisation product in water.

9. The solubilisation product according to claim 1, characterised in that:
   a turbidity of the solubilisation product after 1 hour of storage at 37° C. and pH 1.1 is less than 50 FNU, measured by scattered light measurement with infrared light according to the provisions of the ISO 7027 standard at a 1:50 dilution of the solubilisation product in water.

10. The solubilisation product according to claim 1, wherein the solubilisation product is for use in the treatment of Alzheimer's disease, Friedreich's ataxia and other Ataxia related diseases, lysosomal diseases, cancer, diabetes, atherosclerosis, heart diseases, arthritis or autoimmune diseases.

11. The solubilisation product according to claim 1, wherein the solubilisation product is for use in a method for the treatment of Alzheimer's disease, Friedreich's ataxia and other Ataxia related diseases, lysosomal diseases, cancer, diabetes, atherosclerosis, heart diseases, arthritis or autoimmune diseases, characterised in that:
   the solubilisation product is administered orally, in an amount corresponding to at least 200 mg resveratrol per day.

12. A capsule filled with the solubilisation product according to claim 1, characterised in that:
   the capsule is provided as a soft gelatine capsule, a hard gelatine capsule, a soft gelatin-free capsule, or a hard gelatine-free capsule.

13. A method for the treatment of Alzheimer's disease, Friedreich's ataxia and other Ataxia related diseases, lysosomal diseases, cancer, diabetes, atherosclerosis, heart diseases, arthritis or autoimmune diseases, comprising:
   providing a solubilisation product consisting of resveratrol, an emulsifying agent mixture of polysorbate 80 and polysorbate 20, at least one medium-chain triglyceride (MCT), and tocopherol or mixed tocopherols; and
   orally administering the solubilisation product to a patient.

14. The method according to claim 13, characterised in that:
   the solubilisation product is contained in a capsule; and
   the capsule is provided as a soft gelatine capsule, a hard gelatine capsule, a soft gelatin-free capsule, or a hard gelatine-free capsule.

* * * * *